United States Patent [19]

Stevens et al.

[11] Patent Number: 5,081,231

[45] Date of Patent: Jan. 14, 1992

[54] URANIUM (III) CATALYST FOR THE SELECTIVE DIMERIZATION OF PROPYLENE TO 4-METHYL-1-PENTENE

[75] Inventors: James C. Stevens; William A. Fordyce, both of Midland, Mich.

[73] Assignee: The Dow Chemical Company, Midland, Mich.

[21] Appl. No.: 465,856

[22] Filed: Jan. 16, 1990

Related U.S. Application Data

[62] Division of Ser. No. 226,270, Aug. 1, 1988, Pat. No. 4,960,869, which is a division of Ser. No. 90,268, Aug. 27, 1987, Pat. No. 4,855,523.

[51] Int. Cl.$^5$ .............................................. C07F 5/00
[52] U.S. Cl. ...................................................... 534/11
[58] Field of Search .......................................... 534/11

[56] References Cited

U.S. PATENT DOCUMENTS

| | | | |
|---|---|---|---|
| 2,818,416 | 12/1957 | Brown et al. | 534/11 |
| 3,152,157 | 10/1964 | Shapiro et al. | 534/11 |
| 3,816,372 | 6/1974 | Lugli et al. | 534/11 |
| 3,994,945 | 11/1976 | Poggio et al. | 534/11 |
| 4,072,739 | 2/1978 | Beranger et al. | 423/8 |
| 4,642,337 | 2/1987 | Arnaudet et al. | 534/11 |
| 4,695,669 | 9/1987 | Stevens et al. | 585/511 |
| 4,820,671 | 4/1989 | Chamberlain et al. | 585/511 |
| 4,855,523 | 8/1989 | Stevens et al. | 537/11 |
| 4,960,869 | 10/1992 | Stevens et al. | 534/11 |

*Primary Examiner*—Edward A. Miller
*Attorney, Agent, or Firm*—Marie F. Zuckerman

[57] ABSTRACT

Novel di(poly-substituted cyclopentadienyl)-allylic uranium complexes can be employed to catalyze the dimerization of propylene to form 4-methyl-1-pentene selectively. The novel catalyst complexes can be prepared from novel di(poly-substituted cyclopentadienyl)-U(IV) monohalo monoallylic complexes.

12 Claims, No Drawings

URANIUM (III) CATALYST FOR THE SELECTIVE DIMERIZATION OF PROPYLENE TO 4-METHYL-1-PENTENE

CROSS-REFERENCE TO RELATED APPLICATION

This is a divisional of application Ser. No. 226,270, filed Aug. 1, 1988, now U.S. Pat. No. 4,960,869, which is a divisional of application Ser. No. 090,268, filed Aug. 27, 1987, now U.S. Pat. No. 4,855,523.

BACKGROUND OF THE INVENTION

The present invention relates to a catalyst and process for the dimerization of olefins. More specifically, the invention relates to a new method for the preparation of 4-methyl-1-pentene.

The compound 4-methyl-1-pentene is useful as a monomer or as a comonomer in the production of polyolefins. Typically, 4-methyl-1-pentene is produced via the catalytic dimerization of propylene. Commonly employed catalysts include those containing alkali metals or nickel. Low-selectivity catalysts include thorium nitrate, $WCl_6$, titanium, aluminum alkyls, such as cerium acetylacetonate/aluminum alkyls and certain mixtures of these. Alkali metal catalysts are numerous, but are disadvantageous in that they require high operating temperatures and pressures. Catalysts previously employed for the preparation of 4-methyl-1-pentene via propylene dimerization are all unsatisfactory to the extent that they are not as selective as would be desired. While selectivities to 4-methyl-1-pentene of up to 93 percent have been reported (*Chemical Abstracts*, 100:102722n) using a Na/K-based catalyst, even this is unsatisfactory in view of the difficulty and expense involved in separating 4-methyl-1-pentene from the commonly coproduced $C_6$ olefin and $C_6$ alkane by-products.

Bis(pentahaptopentamethylcyclopentadienyl) (allyl) neodymium and bis(pentahaptopentamethylcyclopentadienyl) (allyl) lanthanum are reported by G. Jeske, et al., *J.A.C.S.*, Vol. 107, pp. 8091–8103 (1985). When reacted with propylene, these materials yield only trace amounts of oligomers with no significant selectivity to 4-methyl-1-pentene. Similarly, bis(pentahaptopentamethylcyclopentadienyl) (allyl) lutetium is proposed as an intermediate in the reaction of bis(pentahaptopentamethylcyclopentadienyl) (methyl) lutetium with propylene by P. L. Watson, et al., *J.A.C.S.*, Vol. 104, pp. 6471–6473 (1982). The products of this chemistry are trace oligomers with no significant selectivity to 4-methyl-1-pentene.

Tris(pentahaptocyclopentadienyl) (allyl) uranium and tris(pentahaptocyclopentadienyl) (allyl) thorium are reported by T. J. Marks et al., *J.A.C.S.*, Vol. 95, pp. 5529-39 (1973) and in Vol. 98, pp. 703-10 (1976), respectively. Pentahaptopentamethylcyclopentadienyltris-(allyl) uranium is described in *Organometallics*, Vol. 2, pp. 963-9 (1983).

U.S. Pat. No. 3,994,945 discloses uranium(IV) tetraallyl compounds and certain halide derivatives thereof. The halide compounds are reported to be useful as catalysts in the stereospecific polymerization of diolefins.

U.S. Pat. No. 3,816,372 discloses uranium(IV) complexes containing metal to carbon $\sigma$ bonds. Ligands such as allyl, cyclobutadienyl and cyclopentadienyl are taught to be coordinated to the metal by $\pi$ bonds. The compounds are disclosed as being useful in the oligomerization of olefins and diolefins, and in the insertion reaction of neutral molecules such as CO and NO.

In view of the deficiencies of prior art methods, it would be desirable to have a catalytic process which would provide improved selectivity to 4-methyl-1-pentene.

SUMMARY OF THE INVENTION

The present invention includes a composition of matter comprising a uranium(III) di(poly-substituted cyclopentadienyl) allylic complex catalyst, a catalyst precursor uranium(IV) di(poly-substituted cyclopentadienyl) (bromo or chloro) allylic complex, a process for preparing the precursor, and a process comprising contacting propylene and the U(III) catalyst under reaction conditions such that 4-methyl-1-pentene is selectively produced. Surprisingly, high selectivity to 4-methyl-1-pentene is obtained using the present invention. The unexpectedly high selectivity advantageously reduces the need for expensive and difficult separation of $C_6$ by-products.

DETAILED DESCRIPTION OF THE INVENTION

A. Dimerization Process and Catalyst

The dimerization process of the present invention advantageously employs a catalyst, propylene and, optionally, a solvent.

Propylene is commercially available, and can be prepared by a number of known methods. In the process of the present invention, propylene can be employed as a gas, a liquid or both.

For the purposes of the present invention, the term "selective" and variations thereof refer to processes which can produce 4-methyl-1-pentene from propylene with a selectivity, as defined hereinafter, of at least 94 mole percent. In the general sense, the term "selectivity" is defined as the moles of 4-methyl-1-pentene in the product stream divided by the total number of moles of reaction products in the reactor effluent stream. Selectivity can also be measured with respect to other $C_6$ olefins or with respect to all $C_6$ compounds in the product stream. High selectivity with respect to other $C_6$ olefins is especially important as the separation of other $C_6$ olefins from 4-methyl-1-pentene is the most difficult separation involved in recovering 4-methyl-1-pentene from the product stream.

The dimerization process of the present invention advantageously employs a novel catalyst comprising a U(III) di(poly-substituted cyclopentadienyl)-allylic complex. Mixtures of catalysts can be employed. The poly-substituted cyclopentadienyl ligands can bear a wide variety of substituents so long as the resulting ligand is substantially inert with respect to propylene, and so long as the substituents are of sufficient size to provide sufficient steric hindrance to make the catalyst composition capable of selectively producing 4-methyl-1-pentene from propylene. Preferred catalysts are represented generally by the formula:

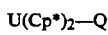

wherein Cp* is a poly-substituted cyclopentadienyl ligand, and Q is an allylic moiety. The allylic moiety can be a $\pi$-bonded or $\sigma$-bonded ligand. Catalysts having π-bonded allylic moieties are represented by the formula:

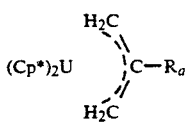

wherein the double bond is delocalized, and catalysts having σ-bonded allylic moieties are represented by the formula:

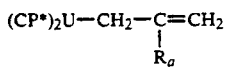

wherein $R_a$ is H, a hydrocarbon moiety or a silicon-containing hydrocarbon moiety. Preferably, $R_a$ is H or alkyl of up to about 6 carbon atoms. Most preferably, $R_a$ is H or methyl. Preferably, each Cp* independently is a moiety of the formula:

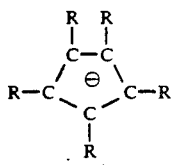

wherein each R independently is H, alkyl of up to about 6 carbon atoms or alkyl substituted silyl such as trimethylsilyl, triethylsilyl, and the like, with the proviso that at least about two R moieties are not H. Preferably, each R is methyl. Examples of catalysts of the present invention include bis-(pentahaptopentamethylcyclopentadienyl) allyl uranium, bis-(pentahapto-bis-(trimethylsilyl)-cyclopentadienyl) allyl uranium and bis-(pentahaptopentamethylcyclopentadienyl) (2-methylallyl) uranium. The most preferred catalyst is bis-(pentahaptopentamethylcyclopentadienyl) allyl uranium.

The term "hydrocarbon" is well-known to those skilled in organic chemistry and refers to a moiety or compound consisting essentially of atoms of carbon and hydrogen. Hydrocarbon moieties can be aromatic or aliphatic; can be saturated or unsaturated; can have carbon chains which are branched, cyclic or straight, and can have mixtures of these attributes. Preferred hydrocarbon moieties have up to about 20 carbon atoms and include alkyl, alkenyl, aryl, alkaryl or aralkyl. Examples of hydrocarbon moieties include methyl, ethyl, butyl, phenyl, allyl, benzyl and the like. Lower alkyl and lower alkenyl of up to about 6 carbon atoms are more preferred. The term "silicon-containing hydrocarbon" refers to hydrocarbons which contain at least one atom of silicon. Examples of silicon-containing hydrocarbon moieties include trimethylsilyl methyl, bis-(trimethyl-silyl)methyl and the like.

It is preferred that the catalyst be employed in a substantially inert environment, i.e., an environment having propylene as essentially the only reactive component of a feed stream. The catalyst of the present invention is, in its purified form, sensitive to air, water and other materials which provide a source of acidic hydrogens. Accordingly, it is preferred that the catalyst compositions of the present invention be maintained in an environment which is substantially inert with respect to degradation of the catalyst.

The catalyst is employed in a catalytic amount. Typically, from about $1 \times 10^{-5}$ to about $1 \times 10^{-1}$ weight parts catalyst are employed per weight part propylene. Preferably, from about $1 \times 10^{-4}$ to about $1 \times 10^{-2}$ weight parts catalyst are employed per weight part propylene.

A solvent is optionally employed in the dimerization process of the present invention. The function of the solvent is to assist in the dissolution of the catalyst. Examples of typical solvents include saturated hydrocarbons, such as pentane, hexane, heptane, octane and other normal or branched saturated paraffins; aromatic hydrocarbons, such as benzene, xylene and other alkyl benzenes; cyclic saturated hydrocarbons, such as cyclopentane, cyclohexane and the like as well as mixtures thereof. Liquid propylene can be employed as a solvent. Toluene is the preferred solvent. The amount of solvent can be varied widely. Typically, from about 0.25 to about 50 weight parts of solvent are employed per weight part of propylene.

The dimerization process of the present invention can be operated at any combination of temperature and pressure at which 4-methyl-1-pentene is selectively produced. Typically, the process is conducted at a temperature ranging from just above the freezing point of the reaction mixture to just below the temperature at which the catalyst decomposes. Preferably, the temperature is from about 10° C. to about 180° C. In general, the reaction proceeds more slowly at lower temperatures. Typically, the process is conducted at a pressure of from about 1 to about 500 atmospheres. In general, the reaction proceeds faster as the pressure increases. The reaction rate is a function of temperature, pressure, catalyst concentration, propylene concentration and the like.

When propylene and the catalyst are contacted under reaction conditions as described hereinabove, 4-methyl-1-pentene is selectively produced. Typically, the selectivity is at least about 94 mole percent, preferably is at least about 96 mole percent, more preferably is at least about 98 mole percent and most preferably is greater than 99 mole percent. This selectivity can be overall selectivity, i.e., based on all products produced, or it can be selectivity with respect to $C_6$ olefins, or all $C_6$ compounds.

B. Catalyst Precursor and Precursor Preparation

The catalyst precursor complex of the present invention can be prepared by contacting an allylic alkylating agent and a bis(poly-substituted cyclopentadienyl) uranium(IV) dihalide in an inert solvent under reaction conditions sufficient to form a uranium(IV) di(poly-substituted cyclopentadienyl) (bromo or chloro) allylic complex.

The preparation of bis-(poly-substituted cyclopentadienyl) uranium(IV) dihalide complexes is well known. For example, the preparation of bis(pentamethylcyclopentadienyl) uranium(IV) dichloride is reported by Juan M. Manriquez, et al. in J.A.C.S., Vol. 100, pp. 3939–3941 (1978). The preparation of di-(bis(trimethylsilyl)cyclopentadienyl) uranium(IV) dichloride is reported by Peter B. Hitchcock, et al. in J. Chem. Soc., "Chem. Commun.," pp. 561–563 (1983). Preferred bis(poly-substituted cyclopentadienyl) uranium(IV) dihalides are represented by the formula $U(Cp*)_2X_2$ wherein Cp* is as defined hereinabove, and X is preferably independently Cl or Br, most preferably Cl.

Allylic alkylating agents are well known in the art and include compounds of the formula:

where Q is an allylic moiety as previously defined, M is a metallic element, and X is an anionic ligand. Preferred anionic ligands include fluoride, chloride, bromide or iodide. The value of n can range from 1 to 4, and m can range from O to a value high enough to satisfy the valence requirements of the metallic element. The allylic alkylating agent can exist as a monomeric species, or as a dimer, trimer, or higher oligomer, and optionally can contain additionally coordinated metal salts. Preferred metallic elements include Li, Na, K, Rb, Cs, Be, Mg, Ca, Ti, Zr, Al, Cu, Ag, Zn, Cd, Hg, Sn and Pb. Silicon, although not generally considered to be a metallic element, can also be employed. More preferred metallic elements are Li, Na, K and Mg. The most preferred allylic alkylating agents are allyl lithium, allyl magnesium chloride, allyl magnesium bromide, 2-methylallyl magnesium chloride, and 2-methylallyl magnesium bromide.

The preferred reaction stoichiometry is one mole of bis(poly-substituted cyclopentadienyl) uranium dihalide to one mole of allylic alkylating agent. Higher molar ratios of allylic alkylating agent to bis(poly-substituted cyclopentadienyl) uranium dihalide can result in over-alkylation and the formation of undesirable bis(poly-substituted cyclopentadienyl) uranium bis(allyls) or even tris(allyl)(polysubstituted cyclopentadienyl) uranium. Over-alkylation is less likely when the allylic moiety has more steric bulk than unsubstituted allyl ($C_3H_5$). For example, an excess of 2-substituted allylic alkylating agent can be successfully employed.

The reaction of the bis(poly-substituted cyclopentadienyl) uranium dihalide with the allylic alkylating agent preferably is conducted in a solvent. Any solvent can be used for the reaction with the proviso that the solvent is substantially inert with respect to degradation of the uranium species as well as the allylic alkylating agent. Ethers are preferred solvents for the reaction of the allylic alkylating agent with the bis(poly-substituted cyclopentadienyl) uranium dihalide. Diethyl ether is the most preferred solvent.

The reaction temperature for the precursor preparation process is not critical. It is preferred that the temperature is below the decomposition temperature of the allylic alkylating agent as well as the decomposition temperature of the uranium species, and that the temperature is high enough for the reaction to proceed at a convenient rate. For the sake of convenience, room temperature is the preferred temperature of the reaction of the allylic alkylating agent with the bis(poly-substituted cyclopentadienyl) uranium dihalide. The reaction preferably is carried out in an environment which is substantially free of oxygen and water.

When a bis(poly-substituted cyclopentadienyl) uranium dihalide and an allylic alkylating agent are contacted under reaction conditions as described hereinabove, a novel precursor uranium(IV) di(poly-substituted cyclopentadienyl)(bromo or chloro) allylic complex is produced. Preferred precursor compounds are represented by the formula $U(Cp^*)_2QX$, wherein Cp*, Q and X are as defined hereinabove.

C. Catalyst Preparation

The catalyst complexes of the present invention can be prepared by contacting a precursor bis(polysubstituted cyclopentadienyl) uranium(IV) monoallylic monohalide with a reducing agent in an inert solvent under reaction conditions sufficient to form a novel uranium(III) bis(poly-substituted cyclopentadienyl) allylic catalyst.

The reducing agent serves to convert the inactive catalyst precursor to the active U(III) catalyst of the present invention. Preferred reducing agents are elemental metals, or amalgams of metals with mercury. Most preferred is sodium analgam. A stoichiometric amount or an excess of the reducing agent can be successfully employed for the reduction process. Preferably, the reducing agent is not able to coordinate to the uranium(III) bis(poly-substituted cyclopentadienyl) allylic product, as additional ligands may be detrimental to the catalytic propylene dimerization process. The use of elemental hydrogen ($H_2$) as a reducing agent is detrimental to the process of the current invention, as hydrogen leads to the formation of trimeric uranium(III) bis(poly-substituted cyclopentadienyl) chloride. See Fagan et al., *Organometallics*, Vol. 1, pp. 170–80 (1982).

A solvent advantageously is employed in the reduction process. Preferred solvents are substantially inert with respect to degradation of the reducing agent as well as the uranium species and function to dissolve the bis(poly-substitued cyclopentadienyl) uranium(IV) monoallylic monohalide as well as the bis(poly-substituted cyclopentadienyl) uranium(III) allyl. Solvents which can coordinate to the product bis(poly-substituted cyclopentadienyl) uranium(III) allyl may be detrimental to the catalytic dimerization process. Hydrocarbons are preferred solvents for the reduction process. Saturated hydrocarbons are more preferred solvents, with pentane and hexane being the most preferred solvents for the reduction process. Solvent mixtures can be employed.

The reaction temperature for the reduction process is not critical. However, it is preferred that the temperature is below the decomposition temperatures of the reducing agent and the uranium species, and that the temperature is high enough for the reaction to proceed at a convenient rate. Room temperature is the preferred temperature of the reduction process for the sake of convenience.

When a bis(poly-substituted cyclopentadienyl) uranium(IV) allylic monohalide and a reducing agent are contacted under reaction conditions as described hereinabove, a novel uranium(III) di(poly-substituted cyclopentadienyl) allylic complex is produced. Preferred catalyst complexes are represented by the formula $U(Cp^*)_2Q$, wherein Cp* and Q are as defined hereinabove.

SPECIFIC EMBODIMENTS OF THE INVENTION

The following examples are given to illustrate the invention and should not be construed as limiting its scope. All parts and percentages are by weight unless otherwise indicated. Cp* represents the pentamethylcyclopentadienyl moiety in the Examples.

EXAMPLE 1

Preparation of UCp*$_2$Cl(allyl)

In an argon-filled inert atmosphere drybox (<0.2 ppm O$_2$), 1.001 g of UCp*$_2$Cl$_2$ (1.728 mmol) is placed in a 500-ml round-bottom flask equipped with a Teflon®-covered stir-bar. The solid UCp*$_2$Cl$_2$ is dissolved in the flask in 100 ml of diethyl ether. A solution of allyl magnesium chloride (26.4 ml, 0.062 moles per liter, 1.637 mmol) in diethyl ether and an additional 25 ml of diethyl ether are added to the flask dropwise over a period of one hour. The resulting mixture is stirred for an additional 15 minutes, then the solvent is removed under vacuum. The remaining brown solid is extracted with 50 ml of refluxing pentane, and then is filtered. The volume of the mother liquor is reduced under vacuum to 20 ml and the solution is allowed to cool in a freezer at −30° C. for one hour. The precipitated dark brown solid is then filtered and dried. The yield is 0.434 g or 48.2 percent. The $^1$H NMR spectrum indicates that the material is UCp*$_2$Cl(allyl).

EXAMPLE 2

Preparation of UCp*$_2$(allyl)

In an argon-filled inert atmosphere drybox, UCp*$_2$Cl(allyl) (0.395 g, 0.675 mmol) is placed in a 25-ml pear-shaped flask with a glass-covered magnetic stir bar and is dissolved in 20 ml of pentane. Sodium amalgam (0.8 percent weight:weight Na:Hg, 1.0 ml, approximately 7:1 mole ratio Na:U) is added with a syringe and the mixture is stirred for 24 hours at room temperature. The mixture is then filtered and the volume of the mother liquor is evaporated to dryness under vacuum. The yield of the green solid is 0.257 g or 69 percent. The $^1$H NMR spectrum is consistent with that expected for UCp*$_2$(allyl).

EXAMPLE 3

A 100-ml stainless steel bomb is taken into an argon-filled inert atmosphere drybox (<0.2 ppm O$_2$) and into the bomb are placed a Teflon®-coated magnetic stir-bar, 9.8 mg of UCp*$_2$(allyl), 25 μl each of heptane and 2,2-dimethylbutane (GC internal standards), and 5.0 ml of toluene as a solvent. The bomb is sealed, removed from the drybox, and set up in a high-pressure cubicle. The gas and vent lines are purged with argon. Liquid propylene (23 g, 45 ml), which is purified in order to remove oxygen, water and other detrimental species, is added to the bomb. Catalysts which can be employed to remove water, oxygen and other paramagnetic impurities are well known in the art, and include such materials as molecular sieves, alumina, silica and finely divided copper on an alumina matrix, such as DOW Q1® catalyst, available from The Dow Chemical Company.

The contents of the bomb are magnetically stirred for 24 hours at 40° C. After 24 hours, the bomb is vented and the contents are analyzed by gas chromatography using a Hewlett-Packard 5880 GC with a 60 meter J & W Narrow Bore Capillary Column bonded with DB-1. The analysis shows 567.6 turnovers (moles of product/moles of uranium) to 4-methyl-1-pentene (0.852 g 4-methyl-1-pentene, 3.70 percent conversion). The overall selectivity to 4-methyl-1-pentene is 98 percent. The major by-products are easily separated C$_9$'s (1.659 mole percent). The selectivity to 4-methyl-1-pentene with respect to other C$_6$'s is 99.653 mole percent.

EXAMPLE 4

A 600-ml stainless steel bomb is taken into an argon-filled inert atmosphere drybox (<0.2 ppm O$_2$) and into the bomb are placed 45.5 mg of UCp*$_2$(allyl), 100 μl each of heptane and 2,2-dimethylbutane, and 50 ml of toluene solvent. The bomb is set up in a high pressure cubicle and filled with 80 g of liquid propylene as described in Example 3. The contents of the bomb are stirred for 16 hours at 60° C. After venting, the contents of the bomb are analyzed as described in Example 3. Analysis reveals 1373 turnovers to 4-methyl-1-pentene (9.57 g of 4-methyl-1-pentene, 12.0 percent conversion) with a selectivity with respect to other C$_6$'s of 99.58 mole percent.

EXAMPLE 5

The procedure is identical to that of Example 4 except that 51 mg of UCp*$_2$(allyl) and 105 g of propylene is used. Analysis by gas chromatography reveals a total of 1275 turnovers to 4-methyl-1-pentene (9.96 g of 4-methyl-1-pentene, 9.48 percent conversion) with an overall selectivity to 4-methyl-1-pentene of 98.05 mole percent. The selectivity to 4-methyl-1-pentene with respect to other C$_6$'s is 99.55 mole percent.

EXAMPLE 6

Preparation of UCp*$_2$Cl(2-methylallyl)

A 100-ml flask is charged with UCp*$_2$Cl$_2$ (512 mg, 0.884 mmole) and 10 ml of diethyl ether. To this solution MgCl(2-methylallyl) (198 mg, 1.729 mmole) dissolved in 10 ml of diethyl ether is added dropwise. The resulting mixture is stirred for 5 minutes, and then the solvents are removed under vacuum to leave a brown residue. The residue is extracted with 70 ml of pentane, and then is filtered. The pentane is reduced in volume under vacuum to yield a brown solid. The solid is filtered and dried. The yield is 420 mg (88 percent). The $^1$H NMR is consistent with that expected for UCp*$_2$Cl(2-methylallyl).

EXAMPLE 7

Preparation of UCp*$_2$(2-methylallyl)

A solution of 252 mg of UCp*$_2$Cl(2-methylallyl) in 25 ml of toluene is stirred in an argon-filled drybox with an excess (250 μl) of 0.8 percent sodium amalgam. After stirring overnight at room temperature, the solvent is removed under vacuum to give a green powder. Hexane (10 ml) is added and the solution is filtered. The hexane is removed under vacuum to give the green product which is identified as UCp*$_2$(2-methylallyl) by $^1$H NMR and mass spectroscopy. The yield is 135 mg (57 percent).

EXAMPLE 8

A 300-ml stainless steel bomb is taken into an argon-filled inert atmosphere drybox and into the bomb are placed 140.6 mg of UCp*$_2$(2-methylallyl), 50 ml of toluene, and 1.920 g of cyclohexane (GC internal standard). The bomb is placed in a high pressure cubicle and is filled with 40.6 ml of liquid propylene as described in Example 3. The contents of the bomb are stirred for 32 hours at 50° C., and samples for GC analysis are periodically taken. The GC analysis reveals that, after 32 hours, there are 638 turnovers to 4-methyl-1-pentene (13.396 g of 4-methyl-1-pentene, 69.4 percent conversion). The overall selectivity to 4-methyl-1-pentene is

What is claimed is:

1. A complex of the formula:

U(Cp*)$_2$Q wherein Cp* is a poly-substituted cyclopentadienyl ligand, and Q is an allylic moiety.

2. The complex of claim 1 wherein each Cp* independently is represented by the formula:

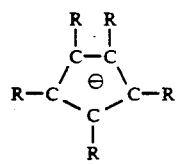

wherein each R independently is H, alkyl of up to about 6 carbon atoms or alkyl substituted silyl with the proviso that at least about 2 R moieties are not H.

3. The complex of claim 1 wherein Q is allyl or 2-methyl-allyl.

4. The complex of claim 2 wherein each Cp* is pentahaptopentamethylcyclopentadienyl.

5. The complex of claim 4 wherein Q is allyl.

6. The complex of claim 4 wherein Q is 2-methyl-allyl.

7. The complex of claim 2 wherein each Cp* is pentahaptobistrimethylsilyl cyclopentadienyl.

8. The complex of claim 1 wherein the allyl moiety is $\pi$-bonded and the complex is represented by the formula:

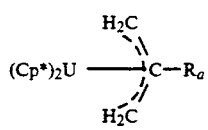

wherein R$_a$ is H, a hydrocarbon moiety of up to about 20 carbon atoms, or a silicon-containing hydrocarbon moiety of up to about 20 carbon atoms.

9. The complex of claim 8 wherein R$_a$ is H or an alkyl moiety of up to about six carbon atoms.

10. The complex of claim 1 wherein the allyl moiety is $\sigma$-bonded and the complex is represented by the formula:

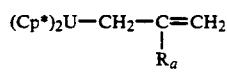

wherein R$_a$ is H, a hydrocarbon moiety of up to about 20 carbon atoms, or a silicon-containing hydrocarbon moiety of up to about 20 carbon atoms.

11. The complex of claim 10 wherein R$_a$ is H or an alkyl moiety of up to about six carbon atoms.

12. The complex of claim 1 wherein each Cp* is pentahaptobistrimethylsilyl cyclopentadienyl and Q is allyl.

* * * * *